United States Patent
Horrell et al.

(10) Patent No.: US 7,270,439 B2
(45) Date of Patent: Sep. 18, 2007

(54) COMPACT LIGHTING SYSTEM ATTACHABLE TO A SURGICAL TOOL AND METHOD OF USE THEREOF

(76) Inventors: Robin S. Horrell, 217 Sage Rd., Louisville, KY (US) 40207; David Bibelhausen, 2256 Hunt Ct., Maineville, OH (US) 45039; Mickey M. Karram, 8700 Old Indian Hill Rd., Cincinatti, OH (US) 45223; John F. Love, 7 Pinehurst Cir., Monroe, NY (US) 10950

( * ) Notice: Subject to any disclaimer, the term of this patent is extended or adjusted under 35 U.S.C. 154(b) by 0 days.

(21) Appl. No.: 11/152,311

(22) Filed: Jun. 13, 2005

(65) Prior Publication Data

US 2006/0291195 A1    Dec. 28, 2006

(51) Int. Cl.
*F21S 2/00* (2006.01)

(52) U.S. Cl. .................. 362/119; 362/294; 362/373; 362/572; 362/804

(58) Field of Classification Search .............. 362/109, 362/119, 120, 808, 294, 373, 572, 804
See application file for complete search history.

(56) References Cited

U.S. PATENT DOCUMENTS

| | | | |
|---|---|---|---|
| 4,348,715 A * | 9/1982 | Christensen et al. | 362/109 |
| 6,129,662 A * | 10/2000 | Li et al. | 600/182 |
| 6,428,180 B1 * | 8/2002 | Karram et al. | 362/119 |
| 6,991,351 B1 * | 1/2006 | Petrick | 362/373 |
| 2006/0146535 A1 * | 7/2006 | Yuen | 362/260 |

* cited by examiner

*Primary Examiner*—Sandra O'Shea
*Assistant Examiner*—James W Cranson, Jr.
(74) *Attorney, Agent, or Firm*—Synnestvedt & Lechner LLP

(57) ABSTRACT

A compact, self-contained lighting system is attachable to a surgical tool to enable a user to selectively direct light at a site where the tool is to be applied. The system has a power unit that may contain rechargeable power cells, a malleable electrical connection element, and a light-emitting element powered thereby to emit high intensity white light, preferably from an LED. The system ensures against tissue damage due to inadvertent overheating by continuously removing byproduct heat from the light-emitting element, via the connection element, to the power unit with portions of each of these components serving as respective heat sinks and/or as thermal conduits to facilitate this process. The removed heat is dissipated to the ambient atmosphere, the surgical tool and even the user, and permits safe prolonged operations in confined regions of a patient's body.

28 Claims, 11 Drawing Sheets

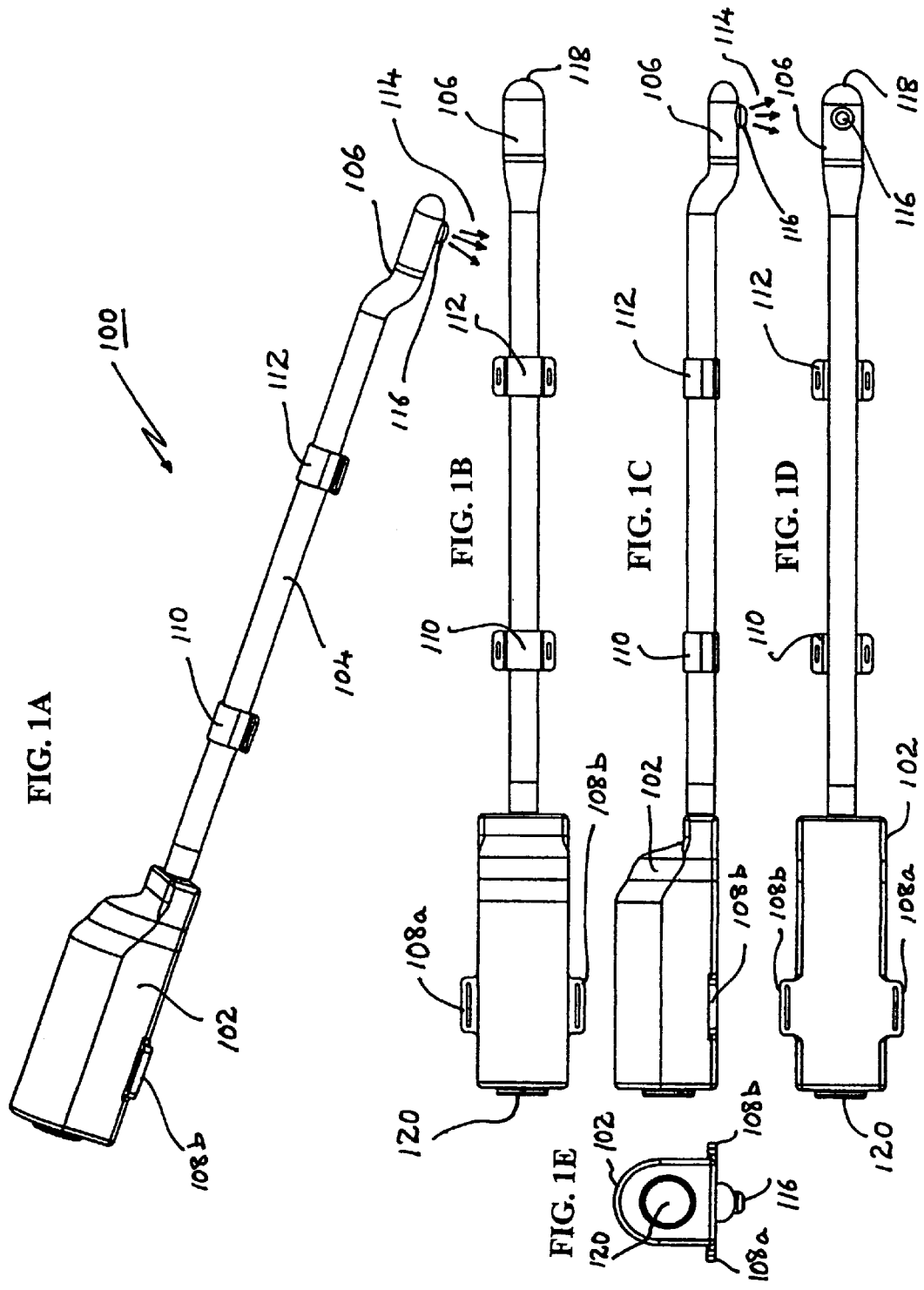

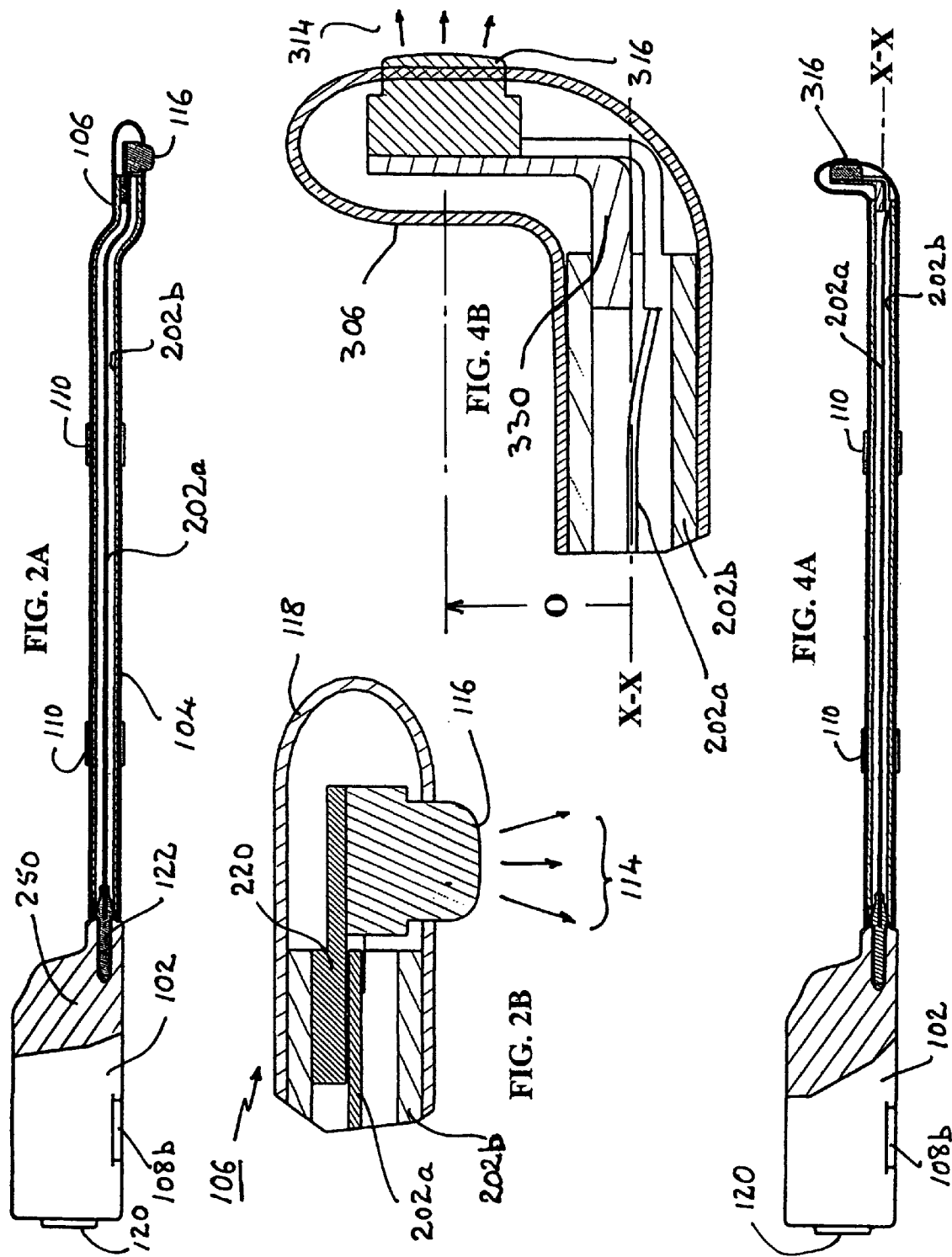

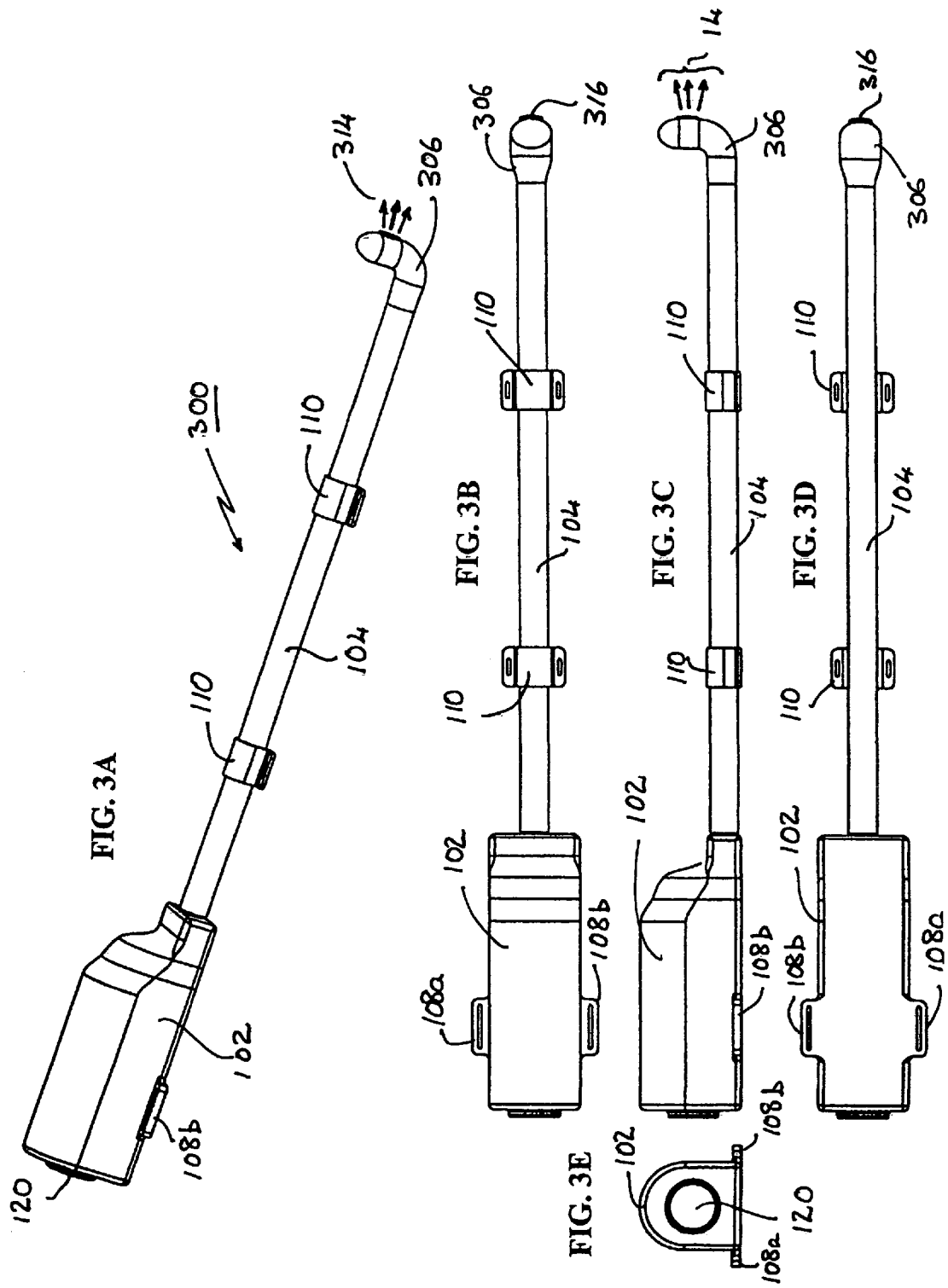

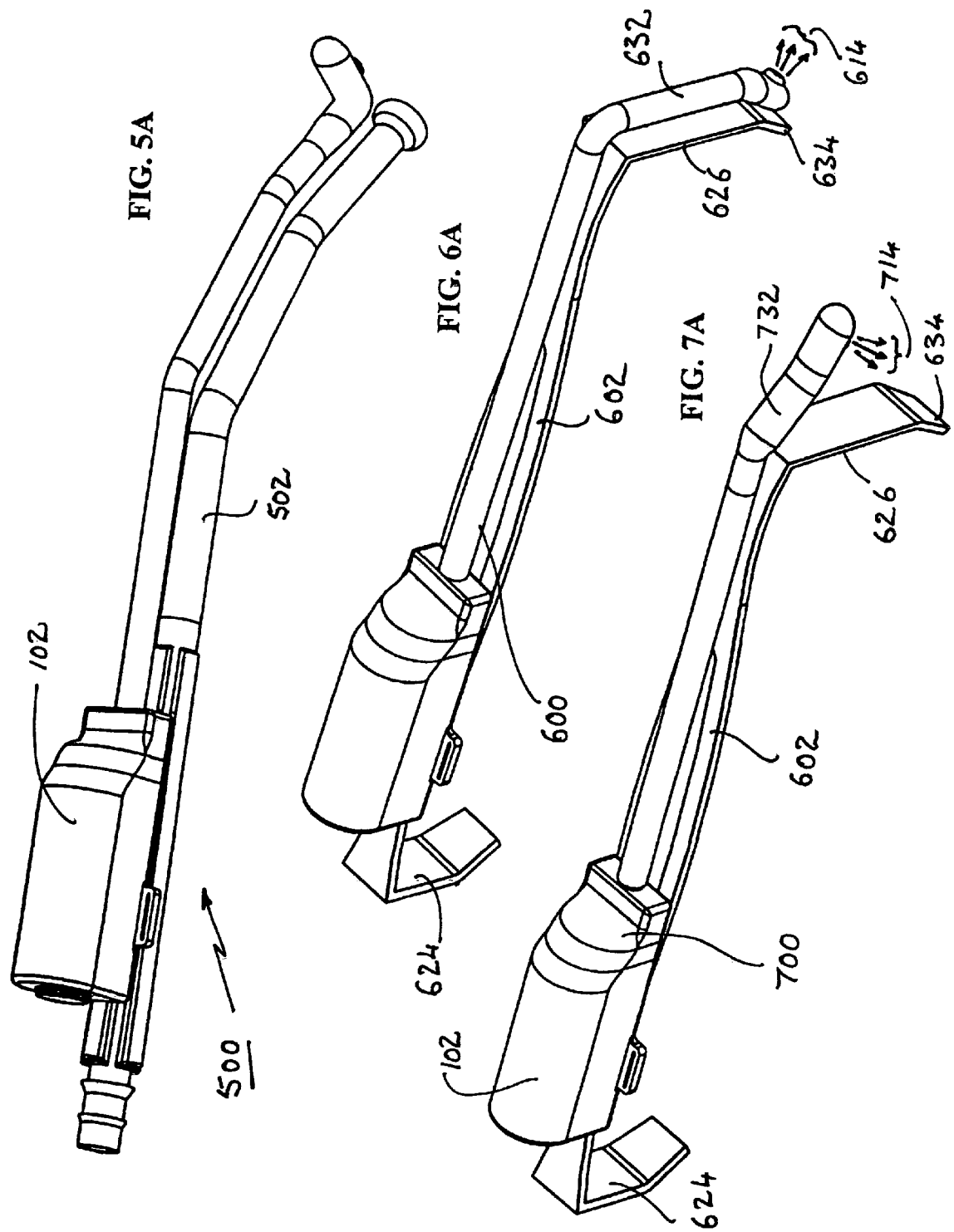

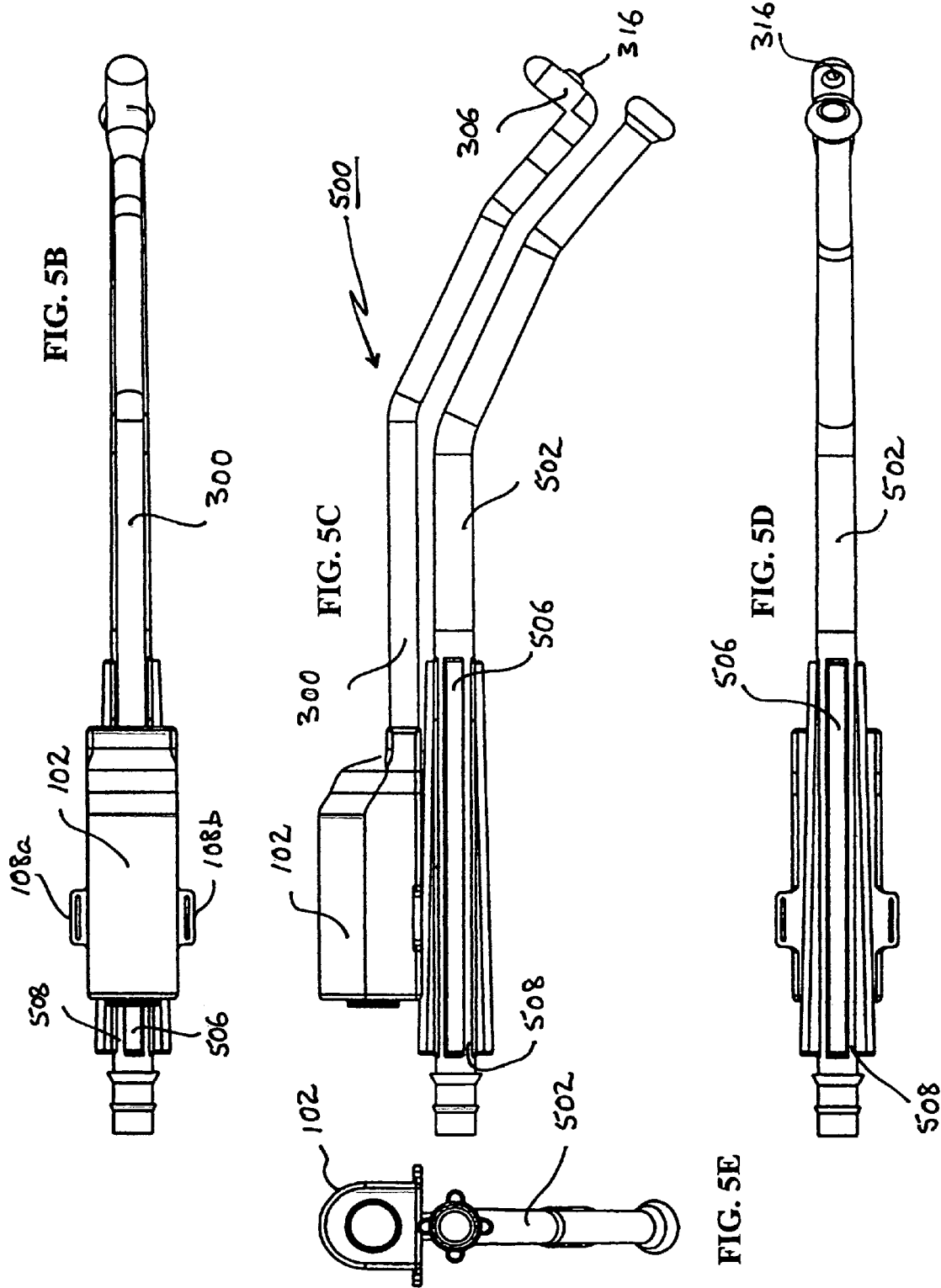

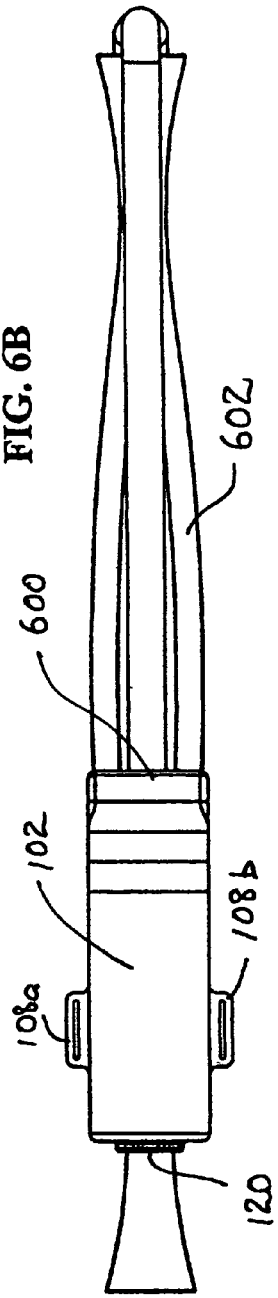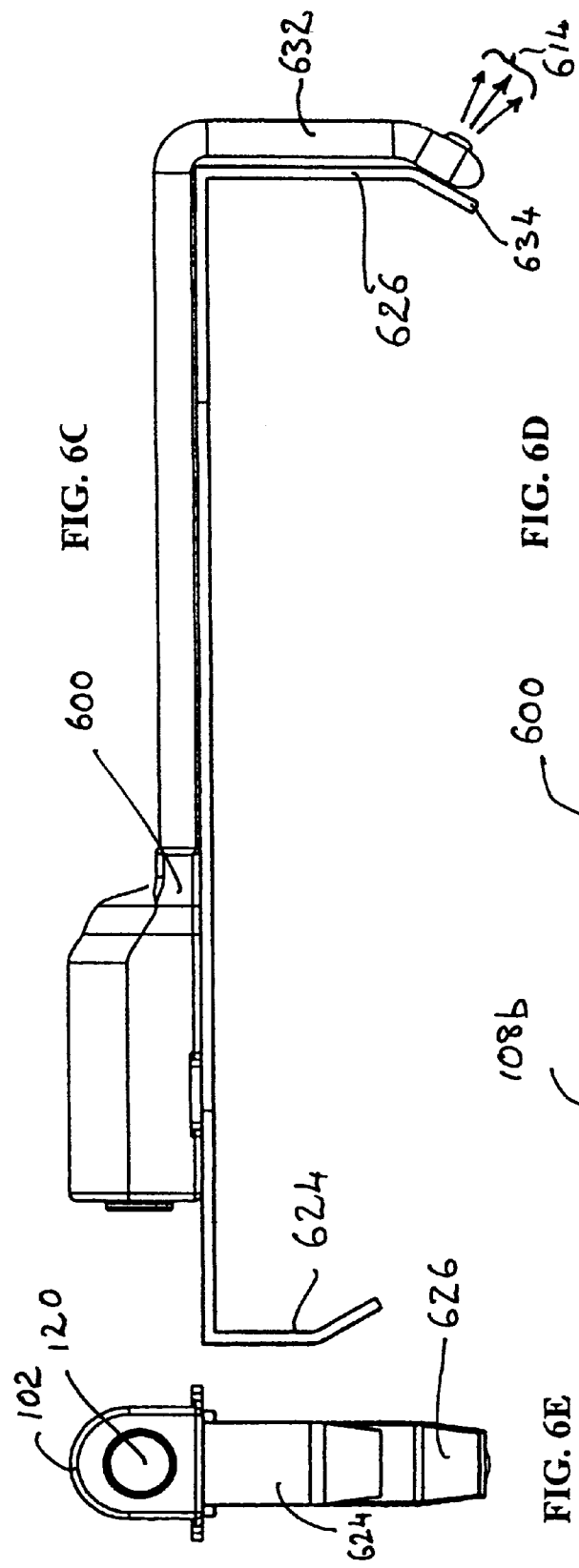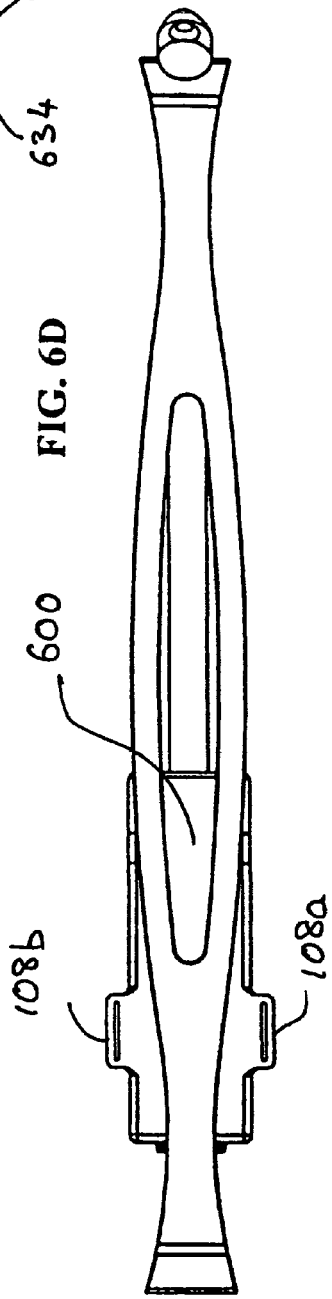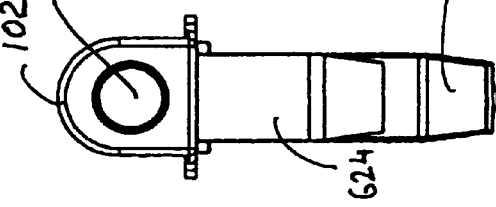

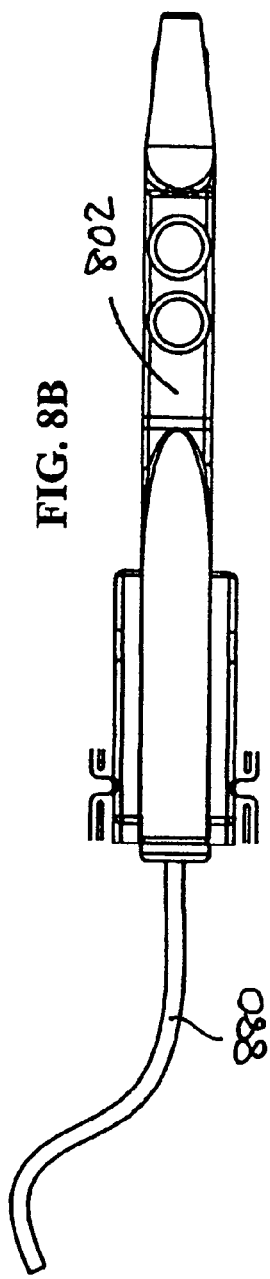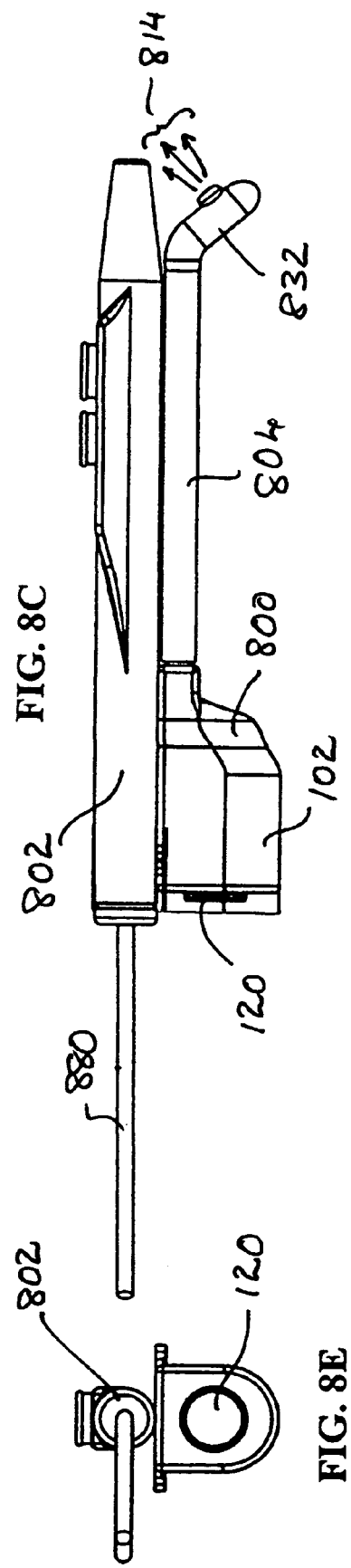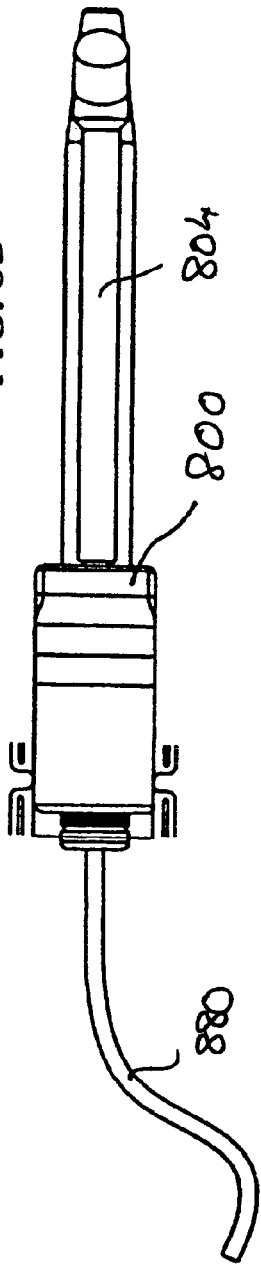

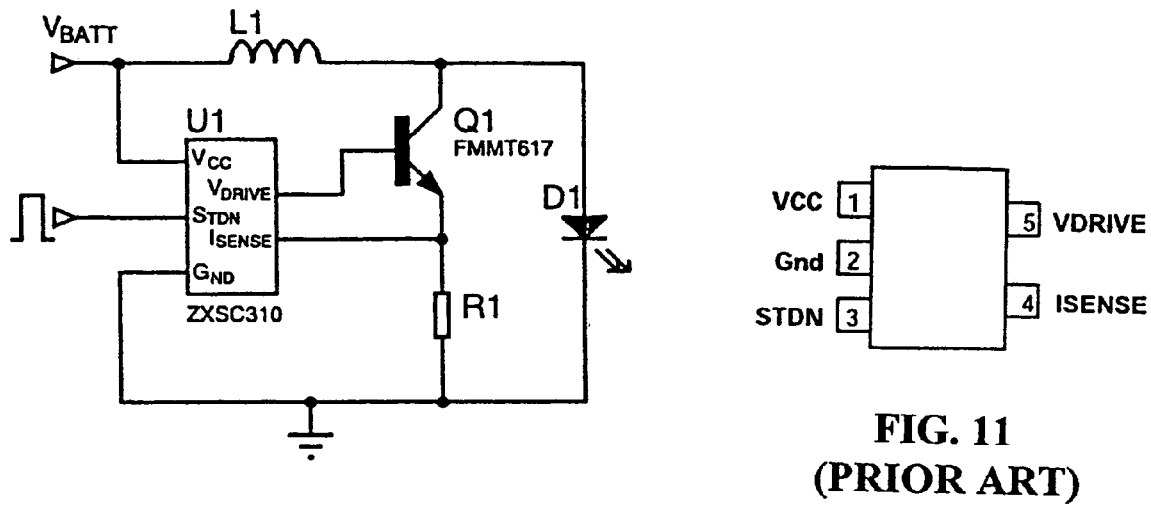
**FIG. 10
(PRIOR ART)**
**FIG. 11
(PRIOR ART)**
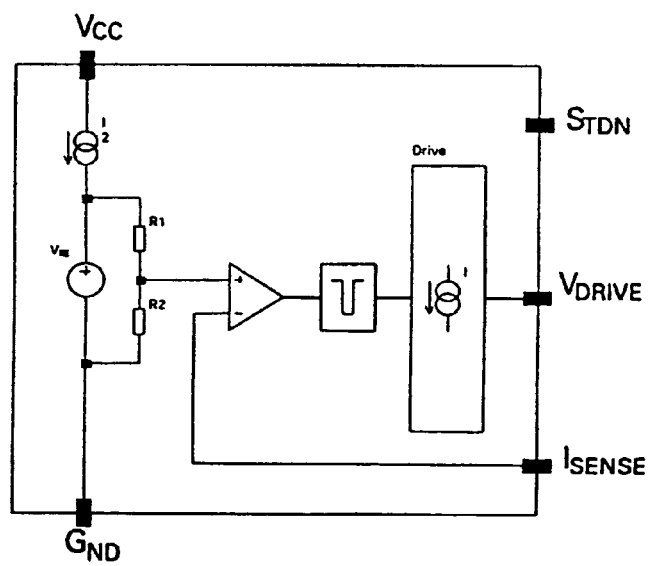
**FIG. 12
(PRIOR ART)**

COMPACT LIGHTING SYSTEM ATTACHABLE TO A SURGICAL TOOL AND METHOD OF USE THEREOF

FIELD OF THE INVENTION

This invention relates to a lightweight, compact lighting system configured to be readily attachable to a hand-held surgical tool to provide lighting of a surgical site during use of the tool. More particularly, the invention relates to a lightweight, compact, self-powered, optionally modular to be partially reusable, lighting system that can be readily attached to any of a variety of known hand-held surgical tools to provide the user clear, consistent and selectively directed white lighting of a surgical site at which the tool is to be applied. Heat incidental to generation of light is removed away from the light-generating portion of the lighting system to ensure safe prolonged operation.

BACKGROUND OF THE RELATED ART

Surgeons operating in confined regions of a patient's body, e.g., in an ear, throat or vagina, often encounter difficulty in obtaining adequate, clear, safe lighting of the operational site—especially during prolonged operational procedures. This is also the case when surgery is performed in other confined regions such as the mouth, abdomen or pelvis. The mounting of a light source on a surgeon's forehead, light sources manipulated by an assistant, and other known solutions generally are not satisfactory—especially where avoidance of shadowing and correct angle of incidence are important considerations. Neither is the provision of a light source mounted to the surgeon's wrist or finger, or even on the surgical tool itself, if the lighting elements are bulky or if either the lighting or electrical power is conveyed by trailing fiber-optic cables, wires or other arrangements that tend to limit the surgeon's freedom of movement or might become entangled where multiple light sources are required. Furthermore, the provision of clear white light of sufficient intensity for periods exceeding more than a few minutes poses the problem that portions of the lighting system may attain unacceptably high local temperatures and may accidentally cause tissue damage to either the patient or to members of the surgical team. Another concern always present if oxygen is being supplied to the patient is the danger of igniting materials contacted by the hot light source. There is therefore a clearly felt need for a lightweight, compact, readily adaptable lighting system to facilitate safe, satisfactory lighting for surgeons.

Factors that must be considered in developing an answer to this need include affordability both initial and in the long term (i.e., the retail price of any lighting system and the feasibility of sterilization and reuse of at least some of the components, inclusion of rechargeable power sources, etc.), versatility of the solution (i.e., its adaptability for use with a wide variety of known or existing surgical tools), its reliability and its acceptability to prospective users.

The most relevant art is believed to be U.S. Pat. No. 6,428,180, to Karram et al., titled "Surgical Illumination Device and Method of Use", which teaches a compact, self-powered, selectively-mountable lighting unit that meets many but not all of the requirements reviewed above, e.g., it does not include specific means to deliberately transfer heat away from the light-generating element during operation of the unit. One example of how to conduct away heat from a relatively high-temperature zone in a lighting device is suggested in U.S. Pat. No. 6,834,977 to Suehiro et al., titled "Light Emitting Device", in which a plurality of LED elements are operated on a common lead from which heat is conducted to another common lead on an opposite side of a substrate. The use of filters in an overhead lighting system, to selectively permit transmission of visible light while impeding transmission of heat energy radiation, i.e., long wavelengths, is suggested in U.S. Pat. No. 6,443,596, to Bulko et al., titled "Surgical Light Apparatus With Improved Cooling". U.S. Pat. No. 6,675,483, to Bond et al., titled "Combination Barbecue Tool", teaches a combination tool in which by the use of locking means a single handle may be selectively attached to any of a variety of implements.

It is considered that these and other such references do not, even when considered together, teach how to fully address the problem solved by the present invention as described below with reference to the attached drawings.

SUMMARY OF THE INVENTION

It is a principal object of the present invention to provide a lightweight, compact, self-powered, safely operable lighting system that can be readily attached to a known surgical tool to provide prolonged, clear, consistent lighting at a surgical site.

Another object is to provide a surgeon with a lightweight, compact, safely operable lighting system that can be readily and securely mounted to a conventional surgical tool to provide clear, high intensity, white light at a surgical site in a confined region for prolonged operations.

A related object is to provide a lightweight, compact, self-powered, safely operable lighting system mountable to a known surgical tool to provide a surgeon clear, consistent, high intensity lighting within a selected wavelength range while ensuring that tissues contacted by any part of the lighting system will not suffer damage due to unacceptably high temperature.

Yet another object is to provide a lightweight, compact, self-powered, safely operable lighting system that is modularly constructed to facilitate reuse of selected components to reduce its cost to a user; the system being mountable to a known surgical tool to provide a surgeon clear, consistent, high intensity white light safely for prolonged operations.

A further related object is to provide a lightweight, compact, self-powered lighting system usable with any of a variety of surgical tools, wherein the power supply unit is located away from the operative end of the surgical tool to thereby reduce obstruction of the surgical field of view.

These and other related objects of this invention are realized by providing a lightweight, compact, self-powered, safely operable lighting system that can be readily attached to a known surgical tool, comprising:

a self-contained power unit, comprising first attachment means for attaching to the surgical tool at a predetermined location thereon;

a connection element, connected to the power unit primarily to convey electrical power therefrom;

a light-emitting element, connected to the connection element primarily to receive power from the power unit; and heat transfer means for transferring heat from the light-emitting element via the connection element, whereby a first portion of the transferred heat is conveyed to ambient atmosphere primarily by radiation and convection and a second portion of the transferred heat is conveyed to the power unit, the surgical tool and the user primarily by conduction, to thereby maintain all contactable surfaces of the light-emitting element within a predetermined temperature range at all times during operation of the lighting system.

In a related aspect of this invention there is provided a method for enabling a surgeon to conveniently, comfortably, economically and safely direct clear, consistent, high intensity white light to a surgical site during prolonged operations while continuously removing heat away from the light-emitting element to permit minimization of its size and thus to maximize the surgical field of view.

These and related objects are realized by providing a method for providing safe, convenient and optimum lighting at an operation site where a surgical tool is to be applied, comprising the steps of:

attaching to the surgical tool a self-contained power unit capable of delivering a consistent supply of power, via an electrical conduit that simultaneously serves as a thermal conduit, to a light-emitting element disposed to emit light of a selected intensity in a selected direction relative to the surgical tool;

continually removing heat from the light-emitting element via the thermal conduit at a rate that ensures that no part of the light-emitting element exceeds a predetermined safe temperature during use; and dissipating the removed heat primarily by radiation and convection to the ambient atmosphere and primarily by conduction to the power unit, the surgical tool and the user.

These and other related objects of this invention will be better understood with reference to the attached drawings and detailed description provided below.

BRIEF DESCRIPTION OF THE DRAWINGS

FIGS. 1A, 1B, 1C, 1D and 1E, respectively, are a perspective view, a top plan view, a side view, a bottom plan view and a rear end view of the first embodiment of this invention.

FIG. 2A is a partial longitudinal cross-section view of the first embodiment, and FIG. 2B is an enlargement of the distal end portion thereof.

FIGS. 3A, 3B, 3C, 3D and 3E, respectively, are a perspective view, a top plan view, a side view, a bottom plan view and a rear end view of the second embodiment of this invention.

FIG. 4A is a partial longitudinal cross-section view of the second embodiment, and FIG. 4B is an enlargement of the distal end portion thereof.

FIGS. 5A, 5B, 5C, 5D and 5E, respectively, are a perspective view, a top plan view, a side view, a bottom plan view and a rear end view of the second embodiment, mounted to a suction or aspiration tool of a kind used in conventional surgery.

FIGS. 6A, 6B, 6C, 6D and 6E, respectively, are a perspective view, a top plan view, a side view, a bottom plan view and a rear end view of a third embodiment of this invention, mounted to a retractor tool of a kind used in conventional surgery.

FIGS. 7A, 7B, 7C, 7D and 7E, respectively are a perspective view, a top plan view, a side view, a bottom plan view and a rear enc view of a fourth embodiment of this invention, mounted to a retractor tool of a kind used in conventional surgery.

FIGS. 8A, 8B, 8C, 8D and 8E, respectively, are a perspective view, a top plan view, a side view, a bottom plan view and a rear end view of a fifth embodiment of this invention (shown without a cautery blade) of a kind used in conventional surgery.

FIG. 10 is a circuit diagram of a known and suitable electrical circuit of a kind that enables realization of maximum battery life for the system according to this invention.

FIG. 11 is a schematic pinout diagram for the circuit diagram according to FIG. 10.

FIG. 12 is a block diagram clarifying details of the pinout portion of an integrated circuit according to FIG. 10.

DETAILED DESCRIPTION OF THE PREFERRED EMBODIMENTS

Figure 7B:
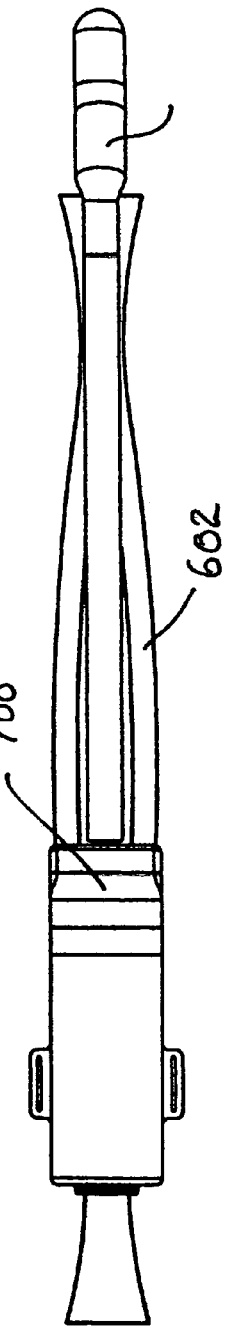

As best seen in perspective view in FIG. 1A, the lighting system per first embodiment 100 of this invention has a compact power unit 102 at a proximal end, connected to a longitudinal connection element 104 which, at its distal end, is attached to a light-emitting element 106.

As further seen in the top and bottom plan views in FIGS. 1B and 1C, respectively, a number of attachment elements such as 108a, 108b on power unit 102, and 110, 112 on connection element 104 may be provided to facilitate attachment of the lighting system to the longitudinal body of a typical surgical tool as discussed below. The number, form and locations of attachment elements is a matter of choice for the manufacturer and user.

Light-emitting element 106 in the first embodiment is of side-lighting kind, i.e., light 114 is emitted sideways relative to the body of the light-emitting element itself from a light source 116 mounted within, access to the inside being available upon removal of sealing element 118 in front.

Power unit 102, likewise, has internal components that may be accessed upon removal of a sealing cap 120 at the rear or at any other convenient location on the body of power unit 102. This cap 120 may be made of a flexible electrically insulating material such as a plastic, and will then allow the user to operate a conventional on-off switch (not shown) that can be actuated by pressure applied there.

The entire lighting system structure may be assembled by conventional friction-or force-fitting of the power unit to the connection element and similar fitting of the latter to the light-emitting element body. Small flexible "O-rings" or the like may be used as gaskets at the respective junctions. Such aspects of the related structure are very common, hence additional discussion is not deemed necessary to instruct persons of ordinary skill in the relevant art. Such an assembly mode would be particularly suitable for a modularized form of the lighting assembly as it would permit a user or vendor to assemble a variety of models, selecting a power unit from a set thereof to obtain different power capacities, selecting a connection element from a set of those to choose a particular length or heat transfer capacity, and a lighting element from yet another set thereof to choose a particular output, wavelength of emitted light, or front or sideways lighting as best suited to a given need. This allows flexibility in customization of the lighting system to meet diverse needs, and makes this invention highly versatile, e.g., adaptable for a very wide range of surgical procedures.

Optionally, the entire lighting system could be assembled and then, using any suitable known manufacturing technique, encased in a thin, sterile, biocompatible, impermeable coating to form a sealed integral item. Numerous suitable plastics materials for such coatings are known that would provide the desired electrical insulation and the thermal conduction capabilities—as discussed below. Such an assembly would be particularly suitable for more or less standard applications, e.g., in providing lighting during urogynaecological surgery on adult female patients.

As now best understood with reference to the longitudinal cross-sectional views per FIGS. 2A and 2B, an electrical pathway is provided between the power unit 102 and light source 116 inside light-emitting element 106 by insulation coated internal wires or other suitable electrical conductors such as 202a, 202b. The outermost layer, or the entire body, of connection element must be made of an electrically insulating but thermally conductive material.

A preferred light source 116 is a light emitting diode (LED) such as commercially available models "Luxeon LXHL-PW01", "Luxeon LXHL-BW03", or the like, that emits high intensity white light and is highly power-efficient. In the present context this means that the preferred lighting, being white, optimizes the user surgeon's viewing and makes minimal demands on the power source, typically compact, lightweight, single use or rechargeable, power cells or batteries.

It should be appreciated that an experienced surgeon can derive valuable information from an accurate viewing of a patient's tissues during a surgical procedure. Clear and consistent lighting of tissues of interest is therefore extremely important. White light is considered particularly useful in revealing subtle gradations of color, hue and condition of tissues that may be healthy, traumatized or diseased. It should also be appreciated that the addition of any lighting system to a known surgical tool will inevitably add to the weight and volume of the combination that will have to be manipulated by the user. The present invention in its various embodiments aims to ensure that the lighting system will be as light in weight, and as small in size, as possible in light of available technology and that it will be configured and disposed to be minimally invasive to the surgeon's field of view. The preferred LEDs will ensure that the preferred white light output will not waver in intensity or color for prolonged periods of use in complex surgery.

It must be noted that there may be circumstances when other than white light may be most suitable, and the modular mode of assembly will easily accommodate such needs by enabling the user to select an appropriate light source while maintaining the familiar feel and heft of the combination of lighting system and surgical tool.

There may be applications where it is most convenient to have the light emitted in a forward rather than a sideways direction relative to the distal end of the surgical tool, and that the light be directed alongside a forwardly extending distal end of the surgical tool, e.g., a scalpel blade or an electrocautery paddle. Lighting for such applications may be best provided via a modified form of the light-emitting element, as best seen in the second embodiment 300 per FIGS. 3A-3E which differs from the first embodiment 100 only in the form of the light-emitting element 306.

As best seen in the enlarged cross-sectional views per FIGS. 4A and 4B, the body of light-emitting element 306 has a right-angle bend at its distal portion, whereby the light source, e.g., LED 316, emits light 314 forwardly and at a point slightly offset relative to the local direction of axis X-X of the connection element 102. The exact amount of this offset "O" is a matter of choice, and the modularity of the present invention allows manufacturers and users of the lighting system to select it to suit themselves very easily.

Referring back to FIGS. 2B and 4B, note that light sources 116 and 316 each have a respective base that serves as a heat sink 220 or 330 respectively. The material for such and other heat sinks ideally should have high heat capacitance and high thermal conductivity. Practicality and considerations of cost and ease of manufacture will determine the actual shapes, thermal capacitances, masses and sizes of the heat sinks and also determine the choice of pure or alloyed metals such as aluminum, copper, gold, brass, beryllium-copper alloy, platinum or titanium, both for the heat sinks and for the electrical conductors. The heat sinks are essentially only thermally conductive masses to which the inevitable byproduct heat from the light-producing activity flows continuously during operation of the light producing LED or the like. The physical configurations, any electrically insulating materials, and the interconnections between the heat sinks, as persons of ordinary skill in the art will appreciate, should be chosen to facilitate heat transfer without adding unduly to the weight of the lighting system.

Highly efficient cooling of such a heat sink is realized by making the electrical conductors already connected thereto simultaneously perform as thermal conduits to flow heat away from the light-emitting element which, in the nature of things, will have the hottest tissue-contacting surface portion of the lighting system. In the structures per FIGS. 2A and 4A, a centrally disposed conductor 202a has the form of a typical insulated wire, and a cylindrical second insulated conductor 202b surrounds it coaxially. In such an arrangement, the thermal mass of outer conductor 202b will be considerably larger than that of inner conductor 202a if both are made of the same material. Outer conductor 202b, therefore, logically also qualifies as a second heat sink that operates cooperatively with the heat sink 220 or 330 depending on the embodiment of interest.

Even with an electrically insulating outer coating, some of the heat flowing via conductor/heat sink 202b will be conducted radially outward to its outermost surface. This radial outflow of heat will then escape to the ambient atmosphere primarily by radiation and/or convection as the surgeon moves the surgical tool and the lighting system around during use. The rest of the heat, however, will flow conductively along heat sink 202b toward the power unit where the thermal mass of its contents and body will serve as yet a third heat sink 250. (See FIG. 2A.) Note that for the modular type of structure there will be conventional kinds of electrical jacks to establish electrical union between the power unit and the connection element and between that and the light-emitting element. Some of the heat flow that reaches this third heat sink 250 in the power unit will then transfer primarily by radiation and convection to ambient atmosphere and some will transfer to the contacting hand of the user primarily via conduction.

An even further cooling advantage can be obtained by employing the surgical tool itself as yet another heat sink. This may be accomplished by providing electrical power from power unit 102 to light source 116 by two electrically insulated wires, and eliminating an external electrically insulating layer on the outside surface of connection element 104. Connection element 104 may then be placed in direct physical and thermal contact with the nearest adjacent surface of the the surgical tool to which the lighting system is to be mounted. This will ensure a thermally-conductive path between connection element 104 and the surgical tool—thereby permitting heat transfer to the latter and engaging the same as yet another heat sink. Naturally, the heat transferred to the surgical tool will in turn be at least partially transferred to the user's hand holding it and to other contacted objects. The key is that by thus engaging the thermal capacitances of the total heat sink system it becomes easier to manage the highest temperatures encountered at any point in the lighting system.

It is an important aspect of this invention in all of its embodiments that this combination of a plurality of cooperating heat sinks manages to maintain the highest temperature anywhere in the lighting system within an acceptable range of temperature so that no harm befalls the patient's tissues, members of the surgical team or surrounding materials even during prolonged operations.

FIGS. 5A-5E depict in various views just how the second embodiment of the lighting system 300 may be used in combination 500 with a conventional suction or aspiration tool 502 of a kind frequently employed during surgery. Particularly noteworthy is the optional provision of arrangement 504 comprising a set of alternating ridges (or flutes) 506 and grooves 508 at the proximal end of the suction tool body to prevent relative rotation between the lighting system and the suction tool. The base portion of the power unit can be configured for this in obvious manner to cooperate with the selected shape of the suction tool in the attachment region. This would make possible the provision of a set of surgical tools having different functions but all having comparable mounting portions at which a particular model of the lighting system could be attached. This would also ensure user-convenience in that the surgeon will experience essentially the same kind of grip regardless of the tool in use.

Alternative attachment means applicable to all embodiments, e.g., adhesion by a double sided tape, the use of loop and hook devices such as "Velcro"™, suction cups, magnetic fasteners, snap fit, spring-loaded clipping mechanisms, and assorted known techniques can be adapted to facilitate the attachment of the lighting system to any known surgical tool. See, for example, U.S. Pat. No. 6,418,180, to Karram et al., cited earlier, which is hereby incorporated by reference for its teaching of such attachment means.

FIGS. 6A-6E depict in various views a third embodiment 600 of this invention, one particularly suitable for use in combination with a conventional bone or tissue retractor 602 having a relatively short lateral end 624 and a longer lateral end 626. This embodiment has a connection element of which a distal end segment 632 can be aligned relative to the retractor body to direct light 614 laterally at an angle and away from the outside of the adjacent longer end 626, as best understood with reference to FIG. 6C. Note that the connection element in any of the embodiments can be made to have a continuous structure or one comprising discrete segments movably connected to each other. If the latter form is utilized, the provision of a particularly dimensioned distal segment 632 as best seen in FIGS. 6A and 6C constitutes a form of structural customization of the invention to suit specific needs.

Figure 7C:
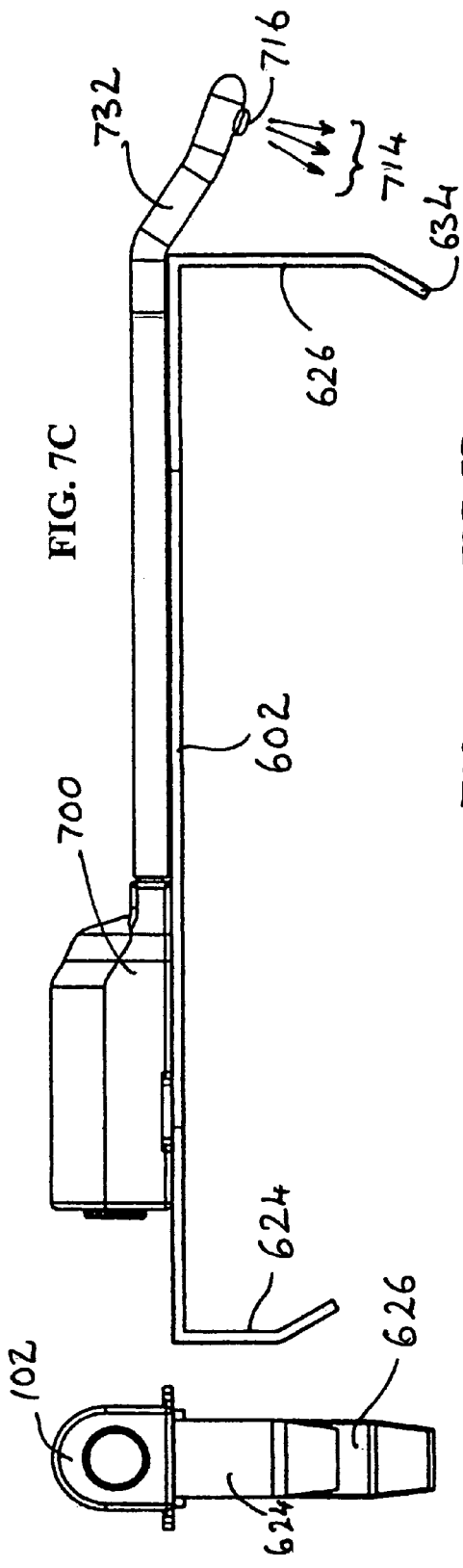
Figure 7D:
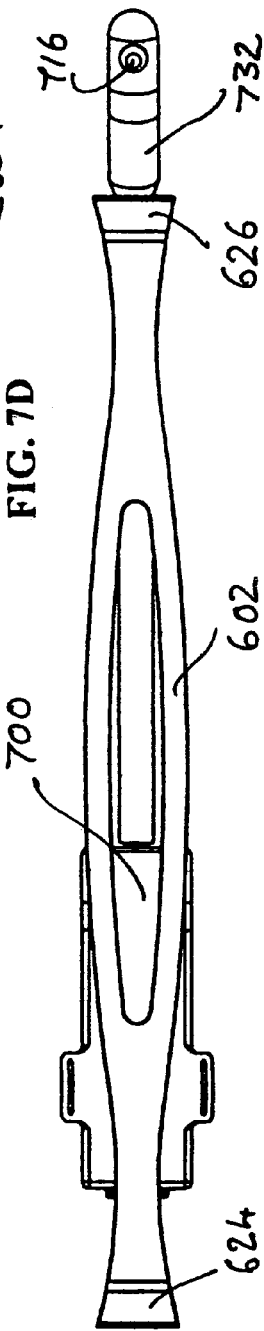
Figure 7E:
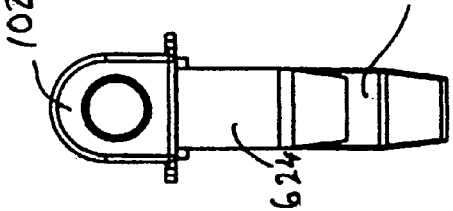
Figure 8A:
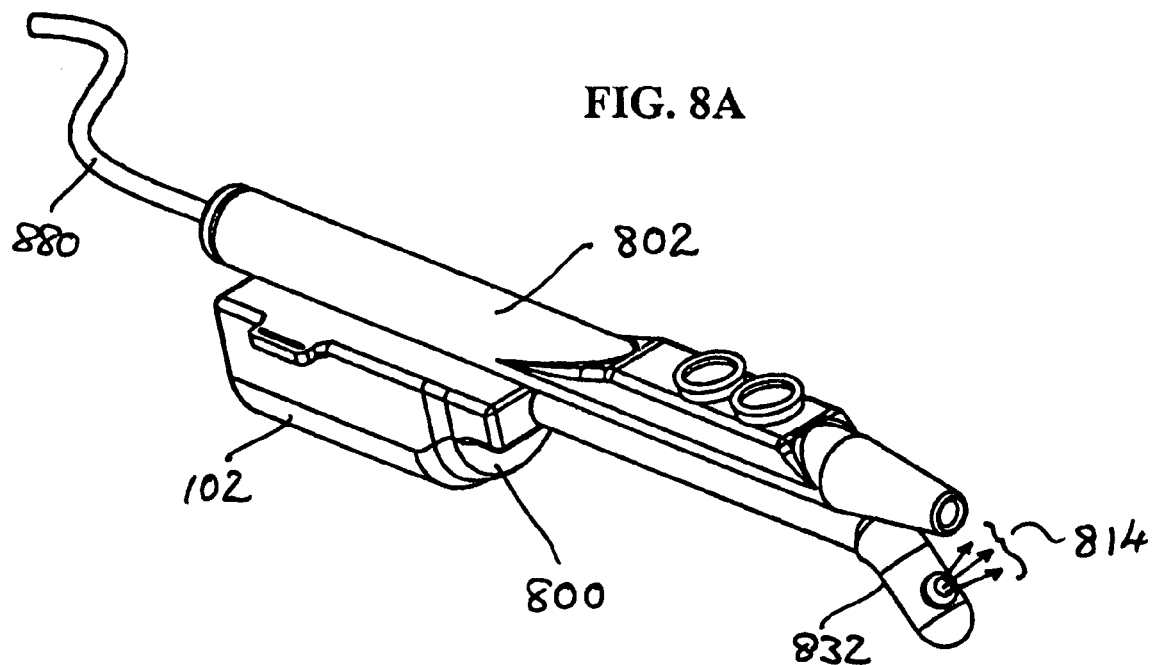

FIGS. 7A-7E depict in comparable views a fourth embodiment 700 as used in combination with the same kind of retractor 602, but this time to direct light 714 toward the extreme distal end 634 of the longer segment 632 as best seen in FIGS. 7A and 7C.

FIGS. 8A-8E depict in comparable views a fifth embodiment 800 as may be used in combination with a conventional electrocautery device 802 (shown without a cautery blade that would extend forwardly to the right in FIGS. 8A-8D). This embodiment differs from the fourth embodiment in that the connection element 804 has a distal segment 832 sized and oriented relative to the distal end of the cautery device 802 so as to direct emitted light 814 toward and forwardly in the region where a cautery blade would be applied to a patient's tissue. Note that in the arrangement at issue the electrocautery device would receive electrical power via a cable 880 entirely independent of the power supply to generate light.

Figure 9:
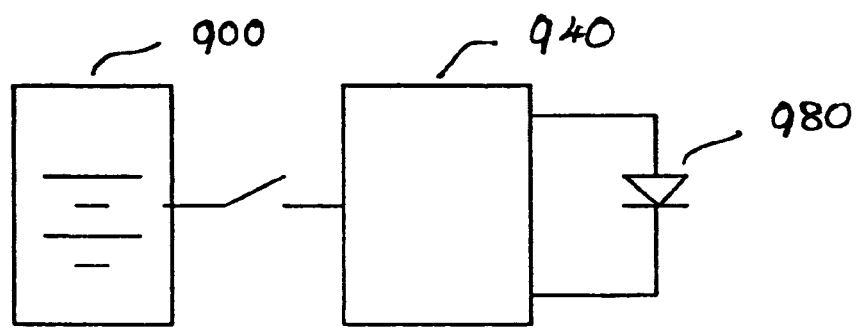
FIG. 9 is a basic schematic diagram of the essential electrical components of the invention.
Figure 15:
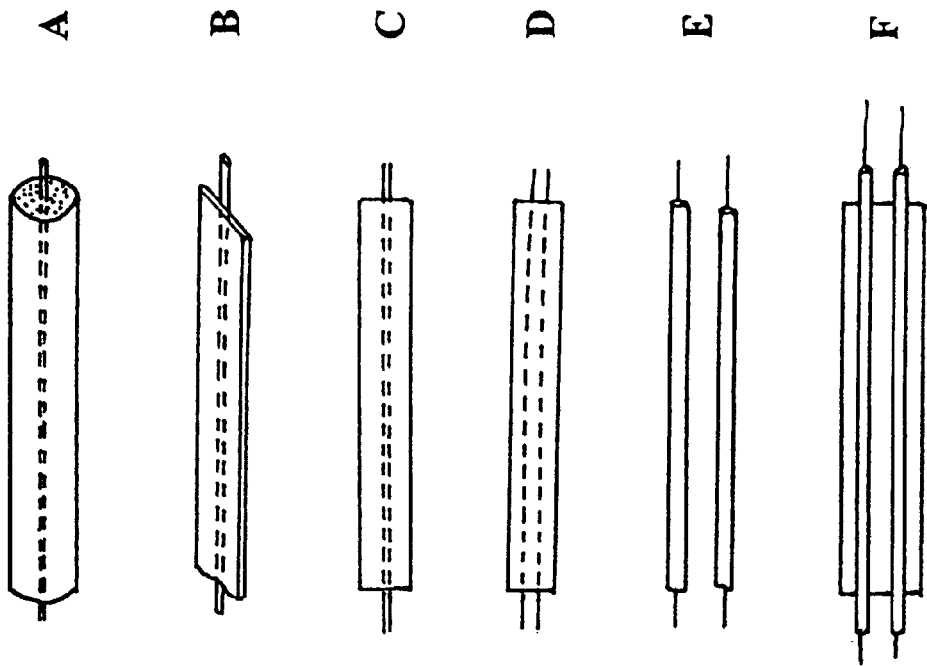
FIGS. 15A-15F are schematics of six optional types of wiring structures considered suitable for portions of the electrical circuits of the system according to this invention.

FIG. 9 is a basic schematic diagram that identifies key portions of the electrical circuit of the lighting system. These are the power source portion 900, the power conversion portion 940 and the light-producing portion 980, respectively.

The power source portion, as generally indicated earlier, will contain at least one power cell. This may be a single use type or rechargeable battery selected to be able to provide a satisfactory flow of direct current at a reasonably steady voltage, i.e., within an acceptable range, although this need not be the rated operating voltage of the chosen LED or other light-producing element.

Provision of the correct voltage to the LED is the purpose of the conversion portion 1040 which converts the electrical energy received from the power source portion 1000 to a constant pulsed current or constant direct current at a voltage required to forward bias the semiconductor junction in the LED.

A preferred power source is a single primary lithium battery cell with a nominal 3.2 v delivery rating. Use of a primary single use cell of this type simplifies the design and operation of the lighting system since no provision is required for circuit elements to enable recharging of the cell. This is particularly suitable for a totally sealed integral system that is intended to be entirely disposable after a single term of use until the power source is exhausted. Economies of scale in manufacture may make such systems highly affordable, but care must be exercised in the eventual disposal of the power cell or unit to ensure compliance with environmental regulations intended to prevent heavy metal pollution and possibly for recycling and recovery of valuable ingredients of the system. The power cell itself may be of a kind that is readily removable, rechargeable and/or replaceable. Use of a single cell also assists in limiting the volume and weight, and thus enhances the portability of the lighting system as a whole. Use of a single cell power source is also desirable for modularized systems because only the power source portion needs to be discarded and the other parts of the system may be sterilized for reuse.

An obvious option is to use rechargeable cell(s) of the kind commonly used in computers, cell phones, DVD players, electric shavers, and the like. The technology is constantly evolving, and many such cells are currently available, hence a suitable one can be readily chosen by persons of ordinary skill in the art to ensure adequate power supply for specific applications. Recharging can be accomplished in the same way as is done for known devices. This option therefore is highly suitable for totally sealed integral lighting systems which can in practice be used, sterilized, recharged within a thin film sterile packaging, and made available for reuse. Rechargeable cells typically have a long but not limitless life and will eventually have to be replaced but, despite higher initial costs, economies of scale may make them preferable for large users like major hospitals or emergency centers that support extensive surgical practices.

The power conversion portion 940 performs a voltage boost function. This is necessary because the most suitable white light LEDs typically have a forward bias voltage higher than the 3.2 v nominal voltage of a lithium cell. Power conversion portion 1040 must provide a constant current, at a voltage that fully forward biases the LED, to ensure the surgeon steady, clear and consistent lighting throughout the anticipated period of use. This must be done regardless of any decline in the output voltage from the power cell(s) as the stored energy therein is depleted to exhaustion.

The preferred LEDs typically have a forward bias voltage of 3.4 v, and for such the power conversion portion 940 must deliver a constant current of about 350 mA for a power requirement of 1.2 W. Consumption of this much energy flow by the LED results in significant waste heat that can raise surface temperatures at the light-emitting element to unacceptable levels—particularly if the lighting system is continuously operated for prolonged periods. The previously described heat removal system, employing the necessary electrical conductors as heat conduits, is intended to limit any such temperature rise.

The power conversion portion 940 of the circuit, as preferred, is based on a commercially available device marketed as a ZETEX ZXSC310. This is an integrated circuit which, when combined with a high performance external transistor, enables the production of a high efficiency boost converter for LED driving operations from a battery cell power source. Details of the ZETEX device, and certain variations thereof, may be found in ZETEX Semiconductors Bulletin, Issues 2 and 3, for March 2004. Some of the exemplary circuits are identified as "Prior Art" in FIGS. 11-15 hereof and are briefly described below.

FIG. 10 is a ZETEX circuit designed for maximum battery life in use. The LED in such an application is provided with a pulsed current.

FIG. 11 is an enlarged view of the pinout element identified as "U1" in FIG. 10, and explains the part of the circuit that engages with the single power cell.

FIG. 12 is a block diagram of the controller integrated circuit (IC) which in combination with a high performance external transistor, drives the LED.

Figure 13:
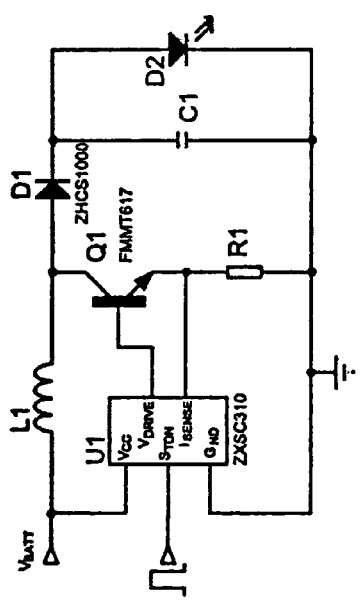
FIG. 13 is a circuit diagram of a known and suitable electrical circuit of a kind that enables realization of maximum brightness of LED light output from the system according to this invention.

FIG. 13 is a modified circuit that provides a maximum brightness solution by rectifying and buffering the DC-DC output made available to drive the LED.

Figure 14:
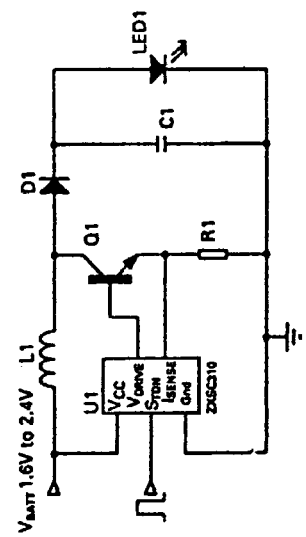
FIG. 14 is a circuit diagram of a known and suitable electrical circuit of a kind that enables optimum operation of a high power white light output LED for the system according to this invention.

FIG. 14 shows the ZETEX ZXSC310 as configured to drive a 1 W LED. This LED has a 180 CD light output from a forward current of 350 mA, and the power source comprises two cells.

Persons of ordinary skill in the electrical arts will immediately appreciate that other such circuits are either commercially available or can be easily designed to suit specific user needs. Additional details therefore are not deemed necessary here.

As noted earlier, employment of electrical conductors and heat sink masses constitutes efficient use of the mass and volume of the lighting system itself to ensure against unacceptably high temperature damage to contacted tissues. Various structural options are available in selecting the electrical conductors, some of which are indicated in FIGS. 15A-15F.

Per FIG. 15A, for example, a single insulated wire is disposed within a malleable conductor serving as an enveloping sheath—particularly suitable for embodiments having a selectively deformable longitudinal stalk-like structure that a user can manipulate to direct light output.

Other similarly flexible and malleable choices include:

per FIGS. 15B and 15C, an insulated electrical wire attached to a flat insulated conductor that will serve as the principal heat conduit;

per FIG. 15D, two insulated wire conductors attached closely to a thermally conductive element that will provide the principal thermal path for heat removal;

per FIG. 15E, two physically separate insulated conductors that may be twisted about the longitudinal body of connection element 102 by a user, e.g., to modify the lighting delivery to suit personal preferences; and per FIG. 15F, two parallel insulated wires attached to an adherent tape that can be used to dispose them along the body of connection element 102 by a user to suit personal needs, e.g., in arranging the direction of delivered light.

Persons of ordinary skill in the relevant arts will no doubt consider and employ other obvious variations of the structures disclosed and suggested herein. All such modifications and variations are intended to be comprehended within this invention which is limited solely by the appended claims.

The invention claimed is:

1. A lightweight, compact, self-contained lighting system configured to be attachable to a hand-held surgical tool, comprising:
   a self-contained power unit, comprising first attachment means for attaching to the surgical tool at a predetermined location thereon;
   a connection element, connected to the power unit primarily to convey electrical power therefrom;
   a light-emitting element, configured and disposed to maximize a user's field of view, connected to the connection element primarily to receive power from the power unit; and
   heat transfer means for transferring heat from the light-emitting element via the connection element, whereby a first portion of the transferred heat is conveyed to ambient atmosphere primarily by radiation and convection and a second portion of the transferred heat is conveyed to the power unit, the surgical tool and the user primarily by conduction, to thereby maintain all contactable surfaces of the light-emitting element within a predetermined temperature range at all times during operation of the lighting system.

2. The lighting system according to claim 1, wherein:
   the power unit comprises an electrical circuit configured to receive electrical power from at least one power cell within a predetermined first voltage range and to provide the power to the connection element within a second voltage range selected to ensure a predetermined light output from the light-emitting element.

3. The lighting system according to claim 1, wherein:
   the light-emitting element comprises a portion that serves as a first heat sink capable of thermal communication with the connection element.

4. The lighting system according to claim 3, wherein:
   the connection element comprises a portion that simultaneously serves both as a second heat sink capable of receiving heat transferred from the first heat sink and as a thermal conduit between the first heat sink and the power unit.

5. The lighting system according to claim 4, wherein:
   the power unit comprises a portion that serves as a third heat sink capable of receiving heat transferred from the second heat sink.

6. The lighting system according to claim 3, wherein:
   the connection element comprises a portion that maintains thermal contact with the surgical tool to which the lighting system is attached, whereby heat transfer from the connection element to the surgical tool engages the surgical tool as a cooperating additional heat sink.

7. The lighting system according to claim 5, wherein:
the first, second and third heat sinks each comprise a respective material selected to have a high thermal conductivity.

8. The lighting system according to claim 7, wherein:
the high thermal conductivity material selected for the second sink is also malleable, whereby the form of the connection element is physically adjustable by a user to selectively direct light emitted by the light-emitting element.

9. The lighting system according to claim 8, wherein:
the first, second and third heat sinks each comprise a material selected from a group of materials consisting of aluminum, copper, gold, silver, brass, beryllium-copper alloy, platinum and titanium.

10. The lighting system according to claim 1, wherein:
the light-emitting element comprises at least one light emitting diode (LED).

11. The lighting system according to claim 1, wherein:
the light-emitting element comprises a plurality of light-emitting diodes (LEDs).

12. The lighting system according to claim 1, wherein:
the power unit comprises at least one rechargeable power cell.

13. The lighting system according to claim 1, wherein:
the power unit, the connection element and the light-emitting element are physically combined to form a sealed integral unit.

14. The lighting system according to claim 1, wherein:
the power unit, the connection element and the light-emitting element are each formed as electrically connectable individual sealed components, and each is maintained in a sterilized state before use.

15. The lighting system according to claim 14, wherein:
the power unit, the connection element and the light-emitting element are individually sterilizable for reuse.

16. The lighting system according to claim 14, wherein:
the power unit, the connection element and the light-emitting element are each selected from a respective modular set of the same comprising different functional capabilities, whereby a user can assemble a lighting system to suit particular needs.

17. The lighting system according to claim 16, wherein:
the modular set of power units comprises individual power units capable of providing a variety of power outputs, a variety of output voltages and a variety of attachment means compatible with different surgical tools.

18. The lighting system according to claim 16, wherein:
the modular set of connection elements comprises individual connection elements capable of providing a variety of electrical and thermal conductances.

19. The lighting system according to claim 16, wherein:
the modular set of light-emitting elements comprises individual light-emitting elements capable of providing a variety of orientations of emitted light output, a variety of light output intensities, and a variety of emitted light wavelength ranges.

20. The lighting system according to claim 1, wherein:
the connection element comprises second attachment means for attaching to the surgical tool.

21. The lighting system according to claim 1, wherein:
the first attachment means comprises one selected from a group consisting of adhesive, loop and hook, flexible tie, suction cup, snap, friction fit, tongue and groove, and magnetic attachments.

22. The lighting system according to claim 1, wherein:
the second attachment means comprises one selected from a group consisting of adhesive, loop and hook, flexible tie, suction cup, friction fit, tongue and groove, and magnetic attachments.

23. A compact lighting system attachable to a surgical tool to provide high intensity light of selected wavelength directable by a user to light a site where the tool is to be applied, comprising:
a self-contained power unit, comprising first attachment means for attaching to the surgical tool at a predetermined location thereon;
a connection element, connected to the power unit primarily to convey electrical power therefrom;
a light-emitting element, connected to the connection element primarily to receive power from the power unit; and
heat transfer means for transferring heat from the light-emitting element via the connection element, whereby a first portion of the transferred heat is conveyed to ambient atmosphere primarily by radiation and convection and a second portion of the transferred heat is conveyed to the power unit, the surgical tool and the user primarily by conduction, to thereby maintain all contactable surfaces of the light-emitting element within a predetermined temperature range at all times during operation of the lighting system,
wherein
the power unit comprises an electrical circuit configured to receive electrical power from at least one power cell within a predetermined first voltage range and to provide the power to the connection element within a second voltage range selected to ensure a predetermined light output from the light-emitting element,
the light-emitting element comprises a portion that serves as a first heat sink capable of thermal communication with the connection element,
the connection element comprises a portion that simultaneously serves both as a second heat sink capable of receiving heat transferred from the first heat sink and as a thermal conduit between the first heat sink and the power unit,
the power unit comprises a portion that serves as a third heat sink capable of receiving heat transferred from the second heat sink,
the first, second and third heat sinks each comprise a material selected from a group of materials consisting of aluminum, copper, gold, silver, brass, beryllium-copper alloy, platinum and titanium, and
the light-emitting element comprises at least one light emitting diode (LED) that emits white light.

24. The lighting system according to claim 23, wherein:
the power unit, the connection element and the light-emitting element are each formed as electrically connectable individual components.

25. The lighting system according to claim 24, wherein:
the power unit, the connection element and the light-emitting element are individually resterilizable after first use.

26. The lighting system according to claim 24, wherein:
the power unit, the connection element and the light-emitting element are each selected from a respective modular set of the same comprising different functional capabilities, whereby a user can assemble a lighting system to suit particular needs.

27. A method of providing safe, convenient lighting at an operation site where a surgical tool is to be applied, comprising the steps of:
    attaching to the surgical tool, at a user-selected location thereon, a self-contained power unit capable of delivering a consistent supply of power, via an electrical conduit that simultaneously serves as a thermal conduit, to a light-emitting element disposed to emit light of a selected intensity in a selected direction relative to the surgical tool;
    continually removing heat from the light-emitting element via the thermal conduit to ensure that no part of the light-emitting element exceeds a predetermined safe temperature during use; and
    dissipating the removed heat primarily by radiation and convection to the ambient atmosphere and primarily by conduction to at least one of the power unit, the surgical tool and the user.

28. A method of providing safe, convenient lighting at an operation site where a surgical tool is to be applied, comprising the steps of:
    attaching to the surgical tool a self-contained power unit capable of delivering a consistent supply of power and serving as a first heat sink, via an electrical conduit that simultaneously serves as a thermal conduit and a second heat sink, to a light-emitting element comprising a third heat sink, the light-emitting element being disposed to emit light of a selected intensity in a selected direction relative to the surgical tool with minimal obstruction of the user's field of view;
    continually removing heat from the third heat sink via the thermal conduit to ensure that no part of the light-emitting element exceeds a predetermined safe temperature during use; and
    transferring the removed heat via the second and third heat sinks while dissipating portions of the removed heat primarily by radiation and convection to the ambient atmosphere and primarily by conduction to the power unit, the surgical tool and the user.

* * * * *